United States Patent
Kim et al.

(10) Patent No.: US 10,533,086 B2
(45) Date of Patent: Jan. 14, 2020

(54) POLYPROPYLENE RESIN COMPOSITION AND MOLDED PRODUCT THEREOF

(71) Applicants: HYUNDAI MOTOR COMPANY, Seoul (KR); KIA MOTORS CORPORATION, Seoul (KR); LG Hausys, Ltd., Seoul (KR); DAE HA CO., LTD., Dangjin-si, Chungcheongnam-do (KR)

(72) Inventors: Hyun Gyung Kim, Hwaseong-si (KR); Hee Joon Lee, Seoul (KR); Ju-Hyun Ji, Seosan-si (KR); Chun Ho Park, Cheongju-si (KR); Ki Hyun Sung, Ulsan (KR); Kwan Suk Ryu, Asan-si (KR)

(73) Assignees: Hyundai Motor Company, Seoul (KR); Kia Motors Corporation, Seoul (KR); LG Hauseys, Ltd., Seoul (KR); DAE HA Co., Ltd., Chungcheongnam-do (KR)

( * ) Notice: Subject to any disclaimer, the term of this patent is extended or adjusted under 35 U.S.C. 154(b) by 0 days.

(21) Appl. No.: 15/842,146

(22) Filed: Dec. 14, 2017

(65) Prior Publication Data
US 2018/0258270 A1 Sep. 13, 2018

(30) Foreign Application Priority Data

Mar. 10, 2017 (KR) .................. 10-2017-0030703

(51) Int. Cl.
*C08L 23/12* (2006.01)
*C08L 23/14* (2006.01)
*C08L 101/00* (2006.01)
*C08K 5/00* (2006.01)
*G01N 25/48* (2006.01)

(52) U.S. Cl.
CPC ............ *C08L 23/142* (2013.01); *C08K 5/005* (2013.01); *C08L 23/12* (2013.01); *C08L 101/00* (2013.01); *C08F 2800/20* (2013.01); *C08J 2300/22* (2013.01); *C08L 2207/04* (2013.01); *G01N 25/4866* (2013.01)

(58) Field of Classification Search
CPC ...... D05C 17/023; A41D 27/08; B32B 5/022; B32B 7/08; B32B 2556/00; B32B 2305/20; D02G 3/43
See application file for complete search history.

(56) References Cited

U.S. PATENT DOCUMENTS

| | | | | |
|---|---|---|---|---|
| 6,017,990 A | * | 1/2000 | Mizutani et al. | ......... C08K 3/34 524/442 |
| 2014/0242335 A1 | * | 8/2014 | Kondo et al. | ........... C08L 51/06 428/141 |

* cited by examiner

*Primary Examiner* — Nathan M Nutter
(74) *Attorney, Agent, or Firm* — Morgan, Lewis & Bockius LLP

(57) ABSTRACT

A polypropylene resin composition includes: a base resin; a thermoplastic elastomer; and an inorganic filler; a major-axis diameter/minor-axis diameter, which is an aspect ratio of the inorganic filler, is 2 to 8. A molded product includes an injection molding of the polypropylene resin composition. The polypropylene resin composition may simultaneously impart excellent rigidity, impact resistance, and excellent dimensional stability even when applied to a molded product having a small thickness, while maintaining a low specific gravity.

13 Claims, No Drawings

POLYPROPYLENE RESIN COMPOSITION AND MOLDED PRODUCT THEREOF

CROSS-REFERENCE TO RELATED APPLICATION

This application claims under 35 U.S.C. § 119(a) the benefit of priority to Korean Patent Application No. 10-2017-0030703 filed Mar. 10, 2017, the entire content of which is incorporated herein by reference.

TECHNICAL FIELD

The present disclosure relates to a polypropylene resin composition and a molded product thereof.

BACKGROUND

Environmental regulations and improved fuel efficiency require weight reduction for vehicles. The bumpers, having the greatest weight of the plastic automobile parts, could be produced by decreasing the thickness of the part during injection molding. This could reduce the weight of the bumper, reduce production cost and improve productivity. However, when the thickness of the part is decreased, mechanical properties deteriorate, and accordingly, the assembling workability on automobile production lines and the stability in the case of an accident deteriorate. Therefore, in order to secure the stability in the case of an accident while reducing energy consumption required for injection molding, there is a need for developing a material having high fluidity, high rigidity, and excellent dimensional stability for an ultra-thin film of a part.

The above information disclosed in this Background section is only for enhancement of understanding of the background of the invention, and therefore, it may contain information that does not form the prior art that is already known in this country to a person of ordinary skill in the art.

SUMMARY OF THE DISCLOSURE

The present disclosure has been made in an effort to solve the above-described problems associated with prior art.

An aspect of the present disclosure provides a polypropylene resin composition which may simultaneously impart excellent rigidity, impact resistance, and excellent dimensional stability while maintaining a low specific gravity.

In one exemplary embodiment of the present disclosure, a molded product comprising an injection molding of a polypropylene resin composition including a base resin, a thermoplastic elastomer, and an inorganic filler, in which a major-axis diameter/minor-axis diameter, which is an aspect ratio of the inorganic filler, is 2 to 8.

In another exemplary embodiment of the present disclosure, a molded product including an injection molding of the polypropylene resin composition.

The polypropylene resin composition may simultaneously impart excellent rigidity, impact resistance, and excellent dimensional stability even when applied to a molded product having a small thickness, while maintaining a low specific gravity.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

DETAILED DESCRIPTION

Hereinafter reference will now be made in detail to various embodiments of the present disclosure, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The benefits and features of the present disclosure and the methods of achieving the benefits and features will become apparent with reference to Examples to be described below. However, the present disclosure is not limited to Examples to be disclosed below, but may be implemented in various other forms, and the present Examples are only provided for rendering the disclosure of the present disclosure complete and for fully representing the scope of the invention to a person with ordinary skill in the art to which the present disclosure pertains, and the present disclosure will be defined only by the scope of the claims.

In one aspect, the present disclosure provides a polypropylene resin composition including a base resin, a thermoplastic elastomer, and an inorganic filler, in which a major-axis diameter/minor-axis diameter, which is an aspect ratio of the inorganic filler, is about 2 to about 8. The polypropylene resin composition includes a base resin, a thermoplastic elastomer, and an inorganic filler, includes the inorganic filler having an aspect ratio, which is a major-axis diameter/minor-axis diameter of 2 to 8, and thus may simultaneously impart excellent processability and high tensile strength, flexural modulus, impact strength, and dimensional stability even when applied to a molded product having a small thickness, while maintaining a low specific gravity.

The polypropylene resin composition includes a base resin, and the base resin may include one polypropylene resin selected from the group consisting of a propylene homopolymer, a copolymer of propylene and an α-olefin monomer having 2 and 4 to 10 carbon atoms, and a combination thereof.

Examples of the α-olefin monomer having 2 and 4 to 10 carbon atoms include, ethylene, 1-butene, 1-pentene, 1-hexene, 4-methylpentene, 1-heptene, 1-octene, 1-decene, and the like. Specifically, the copolymer of the propylene and the α-olefin monomer having 2 and 4 to 10 carbon atoms may be an ethylene-propylene copolymer. Further, the copolymer of the propylene and the α-olefin monomer having 2 and 4 to 10 carbon atoms may be a block copolymer or a random copolymer. In addition, the copolymer of the propylene and the α-olefin monomer having 2 and 4 to 10 carbon atoms may include an ethylene repeating unit in an amount of about 5 wt % to about 15 wt %. The copolymer includes ethylene in a relatively low content, and thus may enhance the crystallinity of a polypropylene resin and may improve the rigidity and impact resistance of a resin composition including the polypropylene resin.

The base resin may have a crystallinity of about 60% to about 80%. The crystallinity is measured by a differential scanning calorimeter (DSC) analysis, and the base resin may have a crystallinity within the range by specific catalyst and process. Specifically, the base resin may have a crystallinity of about 70% or more. The polypropylene resin composition may simultaneously impart excellent mechanical strength and impact resistance by including a base resin having a high crystallinity as described above. For example, the highly crystalline base resin may simultaneously have a flexural modulus of about 1,700 MPa to about 2,000 MPa, while having an impact strength of about 70 J/m to about 150 J/m.

The base resin may have a melt index of about 50 g/10 min to about 150 g/10 min measured at a temperature of 230° C. and under a load of 2.16 kg in accordance with ASTM D1238. The polypropylene resin composition includes a base resin having a melt index within the range, and thus may impart improved moldability and appearance characteristics, and may simultaneously impart excellent mechanical properties. Specifically, when the melt index of the base resin is less than the range, the flowability deteriorates during an injection molding, and as a result, the molding processability may deteriorate, and when the melt index of the base resin is more than the range, the balance between rigidity and impact resistance of an injection molding may deteriorate.

The polypropylene resin composition may include the base resin in an amount of about 55 wt % to about 65 wt %. When the content of the base resin is less than the range, mechanical properties such as flexural modulus and tensile strength may deteriorate, and when the content is more than the range, the impact strength, and the like may deteriorate.

The polypropylene resin composition includes a thermoplastic elastomer, and thus may impart excellent impact strength, heat resistance, and dimensional stability, and may show excellent injection moldability.

The thermoplastic elastomer may include one selected from the group consisting of a copolymer of ethylene and an α-olefin monomer having 3 to 12 carbon atoms, a styrene-based copolymer, and a combination thereof.

The content of the α-olefin monomer in the thermoplastic elastomer may be about 10 wt % to about 20 wt %. When the content of the α-olefin monomer is less than the range, there may be a problem in that the low temperature impact strength and the impact resistance deteriorate, and when the content is more than the range, there may be a problem in that the rigidity deteriorates.

The α-olefin monomer having 3 to 12 carbon atoms may be one α-olefin compound selected from the group consisting of 1-propene, 1-butene, 1-pentene, 4-methyl-1-pentene, 1-hexene, 1-heptene, 1-octene, 1-decene, 1-undecene, 1-dodecene, and a combination thereof.

The styrene-based copolymer may be one copolymer selected from the group consisting of a styrene-ethylene copolymer, a styrene-butylene copolymer, a styrene-ethylene-propylene copolymer, a styrene-isoprene-styrene copolymer, a styrene-butylene-styrene copolymer, a styrene-ethylene-butylene-styrene copolymer, a styrene-ethylene-propylene-styrene copolymer, a styrene-ethylene-ethylene-propylene-styrene copolymer, and a combination thereof. For example, the styrene-based copolymer may be a block copolymer.

The thermoplastic elastomer may have a melt index of about 1 g/10 min to about 100 g/10 min measured at a temperature of 230° C. and under a load of 2.16 kg in accordance with ASTM D1238. The polypropylene resin composition includes a thermoplastic elastomer having a melt index within the range together with the base resin having a melt index of about 50 g/10 min to about 150 g/10 min, and thus may simultaneously impart excellent rigidity, impact resistance, and excellent dimensional stability even when applied to a molded product having a small thickness.

The thermoplastic elastomer may be included in a content of about 22 parts by weight to about 42 parts by weight based on 100 parts by weight of the base resin. Specifically, when the content of the thermoplastic elastomer is less than the range, the impact strength may deteriorate, and when the content is more than the range, the ductility is reinforced, and as a result, mechanical properties such as flexural modulus may deteriorate, and accordingly, it may be difficult for the thermoplastic elastomer to be used as a part for an automobile.

The polypropylene resin composition includes an inorganic filler having an aspect ratio, which is a major-axis diameter/minor-axis diameter of about 2 to about 8, and thus, may impart reduction in weight and may simultaneously impart excellent mechanical rigidity, impact resistance, and dimensional stability.

The inorganic filler has a plate-shaped structure, that is, a thin-film form having a Z-axis length (thickness) smaller than a cross section represented by X-axis and Y-axis lengths, the longer major-axis diameter in the X-axis and Y-axis lengths may be about 1 μm to about 10 μm, and the aspect ratio, which is the major-axis diameter/minor-axis diameter, may be about 2 to about 8. The inorganic filler improves the flowability of a composition including the inorganic filler, together with an excellent rigidity effect by having an aspect ratio within the range, so that the molding is easily carried out, and excellent dimensional stability may be imparted to a molded product during an injection molding. Specifically, when the aspect ratio of the inorganic filler is less than the range, effects of reinforcing rigidity and impact are significantly reduced, and when the aspect ratio is more than the range, it is difficult to disperse the inorganic filler when a molded material is injected, and as a result, there may be a problem in that a difference in physical properties locally occurs.

The inorganic filler may be included in a content of about 20 parts by weight to about 35 parts by weight based on 100 parts by weight of the base resin. The inorganic filler is included in a content within the range, and thus may impart excellent rigidity, and may simultaneously impart impact resistance and dimensional stability, to a polypropylene resin composition. More specifically, when the inorganic filler is included in a content less than the range, the mechanical rigidity is not sufficiently improved, and as a result, the shape of a molded product formed from the inorganic filler may be easily deformed when the molded product is handled, and when the inorganic filler is included in a content more than the range, there is a problem in that the reduction in weight is slight, the dispersibility of the inorganic filler in the composition may deteriorate, and the impact resistance may deteriorate.

The inorganic filler may be one selected from the group consisting of talc, silica, wollastonite, mica, calcium carbonate, barium sulfate, magnesium oxide, calcium silicate, and a combination thereof.

The polypropylene resin composition may include a master batch-type interfacial bonding agent. That is, the polypropylene resin composition further includes a polypropylene resin surface-modified with an interfacial bonding agent, and thus improves compatibility and bonding property of a resin, an inorganic filler, and the like included in the composition, thereby improving mechanical properties and dimensional stability even in a small content.

Specifically, the surface-modified polypropylene resin may be a polypropylene resin grafted with an unsaturated carboxylic acid or an anhydride thereof. For example, the surface-modified polypropylene resin may be a polypropylene resin grafted with maleic anhydride. At this time, the surface-modified polypropylene resin may be formed by grafting the maleic anhydride in a content of about 1 mol % to about 3 mol %.

The polypropylene resin composition may include the surface-modified polypropylene resin in a content of about 0.7 part by weight to about 4 parts by weight based on 100 parts by weight of the base resin. When the content of the surface-modified polypropylene resin is less than the range, a mechanical property reinforcing effect and dimensional stability may deteriorate, and when the content is more than the range, the impact resistance and resin flowability may deteriorate, and the dimensional stability may deteriorate.

The polypropylene resin composition may further include one additive selected from the group consisting of an antioxidant, a light stabilizer, an antistatic agent, a slip agent, a nucleating agent, a UV absorbent, a dispersant, a coupling agent, a pigment, a colorant, and a combination thereof.

An antioxidant may be one selected from the group consisting of a phenol-based antioxidant, a phosphite-based antioxidant, thiodipropionate, and a combination thereof.

As a light stabilizer, a hindered amine-based light stabilizer, and the like may be used.

An antistatic agent is included in a polypropylene resin composition, and thus decreases static elasticity due to friction, and an additive such as a colorant is uniformly introduced, and as a result, the defect ratio of a production process may be decreased and the production efficiency may be increased. The antistatic agent may be one selected from the group consisting of a low molecular weight-type antistatic agent, a high molecular weight-type antistatic agent, a conductive polymer, and a combination thereof.

A slip agent improves scratch resistance by imparting a slip property to a surface of a molded product which is an injection molding of the polypropylene resin composition, and may be one selected from the group consisting of a siloxane-based slip agent, an amide-based slip agent, and a combination thereof.

In another aspect, the present disclosure provides a molded product including an injection molding of the polypropylene resin composition. The molded product includes an injection molding of the above-described polypropylene resin composition, and may have excellent processability and excellent mechanical properties, that is, high impact strength and flexural modulus and excellent dimensional stability even when applied to a molded product having a small thickness, while maintaining a low specific gravity. The matters on the polypropylene resin composition are the same as those described above.

The molded product may be used for use of an automobile exterior material, such as a bumper, a side sill molding, a door trim spoiler, a side visor, a cowl vent grille, a radiator grille, a side molding, and an end panel garnish.

Specifically, the molded product has a small thickness, and thus may further reduce the weight and simultaneously have excellent mechanical rigidity, impact resistance, and excellent dimensional stability. For example, the molded product may show excellent mechanical strength and impact resistance even in a thickness of less than about 2.5 mm. The molded product may have a thickness of about 2.0 mm to about 2.2 mm. Accordingly, the molded product may be suitable for being used as an exterior material for an automobile, such as a bumper.

Hereinafter, specific examples of the present disclosure will be suggested. However, the Examples described below are only provided for specifically exemplifying or explaining the present disclosure, and the present disclosure is not limited thereby.

EXAMPLES

The following examples illustrate the invention and are not intended to limit the same.

Example 1

A polypropylene resin composition including a base resin being an ethylene-propylene copolymer, an ethylene-octene copolymer, a talc having a major-axis diameter of 2 μm and an aspect ratio of a major-axis diameter/minor-axis diameter of 2, and polypropylene grafted with maleic anhydride was prepared.

At this time, the base resin, the ethylene-octene copolymer, the talc, and the polypropylene grafted with maleic anhydride were mixed at a wt % ratio of 63:18: 16:1.

The polypropylene resin composition was kneaded by using a super mixer or a ribbon mixer, and a pellet was prepared through a water cooling-type cooling by using a twin screw extruder (manufacturer: UNI, diameter: (145) set at a temperature of 180° C. to 220° C., an extruder screw speed of 240 rpm, and an introduction speed of 700 rpm from a hopper. A sample was prepared from the pellet-type composition by using an injection molding apparatus (manufacturer: Niigata Machine Techno Co., Ltd., Clamping force 180 ton) set at 220° C.

Example 2

A polypropylene resin composition was prepared in the same manner as in Example 1, except that a talc having an aspect ratio of a major-axis diameter/minor-axis diameter of 5 was included.

Example 3

A polypropylene resin composition was prepared in the same manner as in Example 1, except that a talc having an aspect ratio of a major-axis diameter/minor-axis diameter of 8 was included.

Comparative Example 1

A polypropylene resin composition was prepared in the same manner as in Example 1, except that a talc having an aspect ratio of a major-axis diameter/minor-axis diameter of 1 was included.

Comparative Example 2

A polypropylene resin composition was prepared in the same manner as in Example 1, except that a talc having an aspect ratio of a major-axis diameter/minor-axis diameter of 9 was included.

Test Examples

<Evaluation>

Test Example 1: Specific Gravity (g/ul)

The specific gravities of the samples prepared in the Examples and the Comparative Examples were measured in accordance with ASTM D792, and the results are shown in [Table 2].

Test Example 2: Melt Index (g/10 min)

The melt indices of the polypropylene resin compositions prepared in the Examples and the Comparative Examples were measured at 230° C. and under a load of 2.16 kg in accordance with ASTM D1238 method, and the results are shown in [Table 2].

Test Example 3: Tensile Strength (MPa)

The tensile strengths of the samples having a thickness of 3 mm prepared in the Examples and the Comparative Examples were measured by setting a crosshead speed at 50 mm/min using ASTM D638 at 23° C., and the results are shown in [Table 2].

Test Example 4: Flexural Strength (MPa)

The flexural moduli of the samples having a thickness of 6 mm prepared in the Examples and the Comparative Examples were measured at a temperature of 23° C. using ASTM D790, and the results are shown in [Table 2].

Test Example 5: Flexural Modulus (MPa)

The flexural moduli of the samples having a thickness of 6 mm prepared in the Examples and the Comparative Examples were measured by setting a crosshead speed at 10 mm/min using ASTM D790 at a temperature of 23° C., and the results are shown in [Table 2].

Test Example 6: IZOD Impact Strength (Jim)

The IZOD impact strengths of the samples having a thickness of 6 mm prepared in the Examples and the Comparative Examples were measured at room temperature (23° C.) in accordance with ASTM D256, and the results are shown in [Table 2].

Test Example 7: Heat Distortion Temperature (° C.)

The thermal deformation temperatures of the samples having a thickness of 6 mm prepared in the Examples and the Comparative Examples were measured by applying a surface pressure of 0.45 MPa using ASTM D648, and the results are shown in [Table 2].

Test Example 8: Moldability

The moldability was measured by performing an evaluation based on a spiral using an injector, and the results are shown in [Table 2].

Test Example 9: Linear Expansion Coefficient ($\times 10^{-5}$ m/m/° C.)

The linear expansion coefficients of the samples prepared in the Examples and the Comparative Examples were measured at a measurement interval of −30° C. to 30° C. by using ASTM E831, and the results are shown in [Table 2].

Test Example 10: Pass Determination

It was judged whether the Examples and the Comparative Examples passed by evaluating physical properties of the Examples and the Comparative Examples based on the following [Table 1]. The following criteria correspond to physical property criteria required for an ultra-thin film exterior material for an automobile.

TABLE 1

| Physical property item | Test method (ASTM) | Determination criteria |
|---|---|---|
| Melt index | D 1238 | 40 or more |
| Specific gravity | D 792 | 0.99 to 1.01 |
| Tensile strength | D 638 | 23 or more |
| Flexural strength | D 790 | 30 or more |
| Flexural modulus | D 790 | 2,300 or more |
| IZOD impact strength | D 256 | 350 or more |
| Heat distortion temperature | D 648 | 120 or more |
| Linear expansion coefficient | E 831 | 6.0 or less |

TABLE 2

|  | Example 1 | Example 2 | Example 3 | Comparative Example 1 | Comparative Example 2 |
|---|---|---|---|---|---|
| Specific gravity | 1.0 | 1.0 | 1.0 | 1.02 | 0.95 |
| Melt index | 44 | 44 | 44 | 38 | 30 |
| Tensile strength | 24 | 24 | 24 | 19 | 18 |
| Flexural strength | 35 | 35 | 35 | 28 | 27 |
| Flexural modulus | 2350 | 2420 | 2570 | 1870 | 1770 |
| IZOD Impact strength | 390 | 392 | 395 | 455 | 395 |
| Heat distortion temperature | 123 | 123 | 123 | 122 | 121 |
| Moldability | Good | Good | Good | Good | Poor |
| Linear expansion coefficient | 5.5 | 5.4 | 5.2 | 6.8 | 6.1 |
| Pass determination | Pass | Pass | Pass | Failure | Failure |

As shown in Table 2, it can be confirmed that the Examples simultaneously had excellent rigidity, impact resistance, and excellent dimensional stability even when applied to a molded product having a small thickness, while maintaining a low specific gravity. Further, the Examples satisfied the pass determination criteria, and thus may be used as an ultra-thin film exterior material for an automobile.

The invention has been described in detail with reference to embodiments thereof. However, it will be appreciated by those skilled in the art that changes may be made in these embodiments without departing from the principles and spirit of the invention, the scope of which is defined in the appended claims and their equivalents.

What is claimed is:

1. A molded product comprising an injection molding of a polypropylene resin composition which includes:
   a base resin;
   a thermoplastic elastomer; and
   an inorganic filler,
   wherein a major-axis diameter/minor-axis diameter, which is an aspect ratio of the inorganic filler, is 2 to 8,
   wherein the inorganic filler has a major-axis diameter of 1 μm to 10 μm, and
   wherein the molded product has a linear expansion coefficient of 5.2 to 5.5.

2. The molded product of claim 1, wherein the base resin comprises one polypropylene resin selected from the group consisting of a propylene homopolymer, a copolymer of propylene, an α-olefin monomer having 2 and 4 to 10 carbon atoms, and a combination thereof.

3. The molded product of claim 1, wherein the base resin has a crystallinity of 60% to 80% measured by a differential scanning calorimeter (DSC).

4. The molded product of claim 1, wherein the base resin has a melt index of about 50 g/10 min to about 150 g/10 min measured at a temperature of 230° C. and under a load of 2.16 kg in accordance with ASTM D1238.

5. The molded product of claim 1, wherein the polypropylene resin composition comprises the base resin in an amount of 55 wt % to 65 wt % based on 100 wt % of the total composition.

6. The molded product of claim 1, wherein the thermoplastic elastomer comprises one selected from the group consisting of a copolymer of ethylene and an α-olefin monomer having 3 to 12 carbon atoms, a styrene-based copolymer, and a combination thereof.

7. The molded product of claim 1, wherein the polypropylene resin composition comprises the thermoplastic elastomer in an amount of 12.1 wt % to 27.3 wt % based on 100 wt % of the total composition.

8. The molded product of claim 1, wherein the inorganic filler comprises one selected from the group consisting of talc, silica, wollastonite, mica, calcium carbonate, barium sulfate, magnesium oxide, calcium silicate, and a combination thereof.

9. The molded product of claim 1, wherein the polypropylene resin composition comprises the inorganic filler is in an amount of 11 wt % to 22.75 wt % based on 100 wt % of the total composition.

10. The molded product of claim 1, further comprising: a surface-modified polypropylene resin.

11. The molded product of claim 1, further comprising: a surface-modified polypropylene resin in an amount of 0.385 wt % to 2.6 wt % based on 100 wt % of the total composition.

12. The molded product of claim 10, wherein the surface-modified polypropylene resin is a polypropylene resin grafted with an unsaturated carboxylic acid or an anhydride thereof.

13. The molded product of claim 1, wherein the polypropylene resin composition further comprises one additive selected from the group consisting of an antioxidant, a light stabilizer, an antistatic agent, a slip agent, a nucleating agent, a UV absorbent, a dispersant, a coupling agent, a pigment, a colorant, and a combination thereof.

* * * * *